(12) United States Patent
Masumura (10) Patent No.: US 8,280,494 B2
(45) Date of Patent: Oct. 2, 2012

(54) APPARATUS AND METHOD TO MEASURE A SPECTROSCOPIC CHARACTERISTIC IN AN OBJECT

(75) Inventor: Takahiro Masumura, Tucson, AZ (US)

(73) Assignee: Canon Kabushiki Kaisha, Tokyo (JP)

( * ) Notice: Subject to any disclaimer, the term of this patent is extended or adjusted under 35 U.S.C. 154(b) by 425 days.

(21) Appl. No.: 12/556,693

(22) Filed: Sep. 10, 2009

(65) Prior Publication Data

US 2010/0069750 A1 Mar. 18, 2010

(30) Foreign Application Priority Data

Sep. 16, 2008 (JP) ................. 2008-237027

(51) Int. Cl.
*A61B 5/00* (2006.01)
(52) U.S. Cl. ........ 600/476; 600/437; 600/438; 600/473; 600/477
(58) Field of Classification Search .......... 600/310, 600/407, 438, 473, 476; 356/326
See application file for complete search history.

(56) References Cited

U.S. PATENT DOCUMENTS

| | | | | |
|---|---|---|---|---|
| 6,041,248 | A | 3/2000 | Wang | 600/407 |
| 6,738,653 | B1 | 5/2004 | Sfez et al. | 600/322 |
| 6,957,096 | B2 | 10/2005 | Sfez et al. | 600/407 |
| 2005/0085725 | A1 | 4/2005 | Nagar et al. | 600/437 |
| 2009/0066949 | A1 | 3/2009 | Masumura | 356/326 |
| 2009/0069653 | A1 | 3/2009 | Yoshida et al. | 600/323 |
| 2009/0069674 | A1 | 3/2009 | Masumura et al. | 600/425 |
| 2009/0069685 | A1 | 3/2009 | Nishihara et al. | 600/443 |

FOREIGN PATENT DOCUMENTS

WO WO 02/08740 A2 1/2002

OTHER PUBLICATIONS

Wang, Lihong V. "Ultrasound-mediated biophotonic imaging: A review of acousto-optical tomography and photo-acoustic tomography". Disease Markers 19 (2003,2004) 123-138.*
Wilson et al. "A path-integral model of light scattered by turbid media". J. Phys. B: At. Mol. Opt. Phys. 34 (2001) 1453-1472.*
Li et al. "A calibration method in diffuse optical tomography". J. Opt. A: Pure Appl. Opt. 6 (2004) 844-852.*

(Continued)

*Primary Examiner* — Brian Casler
*Assistant Examiner* — Phong K Huynh
(74) *Attorney, Agent, or Firm* — Fitzpatrick, Cella, Harper & Scinto (57) ABSTRACT

A measurement apparatus includes a measurement unit configured to irradiate three types of ultrasonic waves and light upon a test region in a test object, and to measure modulated light and non-modulated light, the modulated light being modulated by an acousto-optical effect, and a signal processor configured to calculate a modulation depth that is an intensity of the modulated light divided by an intensity of the non-modulated light for the one, and at least one of a scattering characteristic and an absorption characteristic of the test region in the test object by utilizing a first change rate of the modulation depth to an amplitude of the one or an amount corresponding to the first change rate, and a second change rate of the modulation depth to a frequency of the one or an amount corresponding to the second change rate.

8 Claims, 8 Drawing Sheets

OTHER PUBLICATIONS

J.M. Elazar et al., "Doppler Effect's Contribution to Ultrasonic Modulation of Multiply Scattered Coherent Light: Monte Carlo Modeling", BNSDOCID XP1511127A, *Optics Letters*, vol. 22, No. 2, Jan. 15, 2008, pp. 131-133.

G. Yao et al., "Study of Ultrasound-Modulated Optical Tomography in Biological Tissue With Parallel Detection", BNSDOCID XP10530997A, *Proc. of 22$^{nd}$ Ann. EMBS Int'l Conf.*, Jul. 23-28, 2000, Chicago, pp. 2317-2320.

European Search Report Jan. 5, 2010.

S Sakadzic et al., "Ultrasonic Modulation of Multiply Scattered Coherent Light: An Analytical Model for Anisotropically Scattering Media", *Phys. Rev. E66*, 026603 (2002).

* cited by examiner

APPARATUS AND METHOD TO MEASURE A SPECTROSCOPIC CHARACTERISTIC IN AN OBJECT

BACKGROUND OF THE INVENTION

1. Field of the Invention

The present invention relates to a measurement apparatus and a measurement method.

2. Description of the Related Art

The acousto-optical tomography ("AOT") is a known measurement technique of a spectroscopic (or attenuation) characteristic in a biological tissue (Sava Sakadzic and L. V. Wang, "Ultrasonic modulation of multiply scattered coherent light: An analytical model for anisotropically scattering media," Phys. Rev. E66, 026603 (2002)). The AOT irradiates the coherent light and ultrasonic wave into a biological tissue, and utilizes an effect of light modulation effect ("acousto-optical effect") caused by the interaction between the light and the ultrasonic wave in an ultrasonic irradiation region (test region). The ultrasonic wave generally uses a focused ultrasonic wave, and the ultrasonic focus region is the test region. The AOT obtains the absorption-scattering information in the biological tissue by measuring both signals, i.e., an AC component obtained from the light modulated by the acousto-optical effect, and a non-modulated DC component, by obtaining modulation depth that is a ratio between them, and by mapping the modulation depth.

More specifically, an autocorrelation function of the light modulated by the ultrasonic wave is expressed as follows using a probability density function P(s) of an optical path length "s" [mm], and a scattering field Es:

$$G_1(\tau) = \int_0^\infty p(s) \langle E_S(t) E_S^*(t+\tau) \rangle ds \quad \text{Equation 1}$$

When the coherent light propagates in a homogeneous medium upon which a plane ultrasonic wave is irradiated, an autocorrelation function at time $\tau$ [sec] in an electric field of the scattered light can be written as follows:

$$G_1(\tau) = C \frac{\sinh(z_0 \sqrt{(S_U + S_B + \mu_a) D^{-1}})}{\sinh(L_0 \sqrt{(S_U + S_B + \mu_a) D^{-1}})} \quad \text{Equation 2}$$

Here, "C", $S_u$, and SB are expressed by the following equations:

$$C = \frac{\sinh(L_0 \sqrt{\mu_a D^{-1}})}{\sinh(z_0 \sqrt{\mu_a D^{-1}})} \quad \text{Equation 3}$$

$$S_U = \frac{1}{2}(2n_0 k_0 A)^2 \sin^2(\omega_a \tau/2)(\delta_n + \delta_d) \quad \text{Equation 4}$$

$$S_B = 2\tau/(\tau_0 l^*) \quad \text{Equation 5}$$

The Equation 4 indicates the influence of the ultrasonic interaction, and the Equation 5 indicates the influence by the Brownian movement. Here, D is a diffusion coefficient (=1/$3\mu_s'$) [mm]. $n_0$ is a refractive index of a medium. $k_o$ is the wave number of the light in vacuum [mm$^{-1}$]. $\omega_a$ is an ultrasonic angular frequency (=$2\pi f_a$). l is a mean free path (=$1/\mu_s$) [mm]. $1^* = 1/(1-g)$ [mm]. L is a thickness of the medium [mm]. $L_0 = L + 2l^* \gamma$ is a distance between the two extrapolation boundaries [mm]. $Z_0 = l^*(1+\gamma)$ [mm]. $\gamma = 0.7104$. $\tau_0$ is a relax time of one particle in the Brownian movement [sec]. The following equations are met:

$$\delta_n = \eta^2 k_a^2 l \text{Re}[\hat{j}(\hat{I} - \hat{j})^{-1}]_{0,0} \quad \text{Equation 6}$$

$$\delta_d = (1-g)/3l \quad \text{Equation 7}$$

$$J_{m,n} = (g_m)^{\frac{1}{2}} (g_n)^{\frac{1}{2}} \sqrt{\frac{2m+1}{2}} \sqrt{\frac{2n+1}{2}} \int_{-1}^{1} T(x) P_m(x) P_n(x) dx \quad \text{Equation 8}$$

$$g_m \int_0^\pi f(\cos\theta) P_m(\cos\theta) \sin\theta \, d\theta \quad \text{Equation 9}$$

$$T(x) = \frac{1}{1 - ik_a l x} \quad \text{Equation 10}$$

Here, $\eta(=(\partial n/\partial p)\rho v_a^2)$ is a photoelastic coefficient. $k_a$ is the wave number of the ultrasonic wave [mm$^{-1}$]. $\rho$ is a density [kg/mm$^3$]. $v_a$ is a sound velocity [mm/sec]. $P_j(x)$ is a j-th Legendre polynomial. f(cos $\theta$) is a scattering phase function. Re $[\hat{j}(\hat{I}-\hat{j})^{-1}]$ is a real part of a (0, 0) component of a matrix $\hat{j}(\hat{I}-\hat{j})^{-1}$. The scattering phase function uses, for example, a Henyey-Greenstein function.

The autocorrelation function expressed by the Equation 2 is Fourier-transformed into the following Equation 11 so as to calculate the modulation depth M:

$$I_n = \frac{1}{T_a} \int_0^{T_a} \cos(n\omega_a \tau) G_1(\tau) d\tau \quad \text{Equation 11}$$

$$M = \frac{I_1}{I_0} \quad \text{Equation 12}$$

Here, $T_a$ is an ultrasonic period [sec]. The thus calculated modulation depth M corresponds to a ratio between an AC signal ($I_0$) and a DC signal ($I_1$) obtained by the measurement apparatus. In other words, the modulation depth M is a signal intensity of the modulated light $I_1$ divided by a signal intensity of the non-modulated light $I_0$.

Other prior art include U.S. Pat. Nos. 6,738,653, 6,957,096, and 6,041,248.

The spectroscopic (or attenuation) characteristic contains an absorption (spectroscopic) characteristic and a scattering (spectroscopic) characteristic. An acquisition of the absorption characteristic is demanded because an amount of each of the components, such as hemoglobin, fat, collagen, and water, can be calculated from the absorption characteristic of the light. However, in a form of the modulation depth, the absorption characteristic and the scattering characteristic are not separated from each other and the absorption characteristic cannot be precisely evaluated. The conventional AOT cannot precisely obtain the absorption characteristic.

SUMMARY OF THE INVENTION

The present invention provides a measurement apparatus and a measurement method, which can precisely measure an absorption characteristic and a scattering characteristic of a test object utilizing the AOT.

A measurement apparatus according to one aspect of the present invention is configured to measure a spectroscopic characteristic in a test object using an acousto-optical tomography. The measurement apparatus includes a first measurement unit configured to irradiate at least three types of ultrasonic waves and light upon a test region in the test object, and to measure modulated light and non-modulated light. The three types of ultrasonic waves include an ultrasonic wave having a first frequency and a first amplitude, an ultrasonic wave having a first frequency and a second amplitude, and an ultrasonic wave having a second frequency and a first amplitude. The modulated light is modulated by an acousto-optical effect caused by an interaction between the light irradiated onto the test region and one of the ultrasonic waves. The measurement apparatus further includes a signal processor configured to calculate a modulation depth that is an intensity of the modulated light divided by an intensity of the non-modulated light for each ultrasonic wave, and to calculate at least one of a scattering characteristic and an absorption characteristic of the test region in the test object by utilizing a first change rate of the modulation depth to an amplitude of the one or an amount corresponding to the first change rate, and a second change rate of the modulation depth to a frequency of the one or an amount corresponding to the second change rate.

A measurement method according to another aspect of the present invention is configured to measure a spectroscopic characteristic in a test object using an acousto-optical tomography. The measurement method includes the steps of detecting measuring modulated light and non-modulated light as a result of irradiating at least three types of ultrasonic waves and light upon a test region in the test object, the three types of ultrasonic waves including an ultrasonic wave having a first frequency and a first amplitude, an ultrasonic wave having a first frequency and a second amplitude, and an ultrasonic wave having a second frequency and a first amplitude, and the modulated light being modulated by an acousto-optical effect caused by an interaction between the light irradiated onto the test region and one of the ultrasonic waves, and calculating a modulation depth that is an intensity of the modulated light divided by an intensity of the non-modulated light for each ultrasonic wave, and at least one of a scattering characteristic and an absorption characteristic of the test region in the test object by utilizing a first change rate of the modulation depth to an amplitude of the one or an amount corresponding to the first change rate, and a second change rate of the modulation depth to a frequency of the one or an amount corresponding to the second change rate.

Further features of the present invention will become apparent from the following description of exemplary embodiments with reference to the attached drawings.

DESCRIPTION OF THE EMBODIMENTS

Referring now to the accompanying drawings, a description will be given of embodiments of the present invention.

First Embodiment

Figure 1:
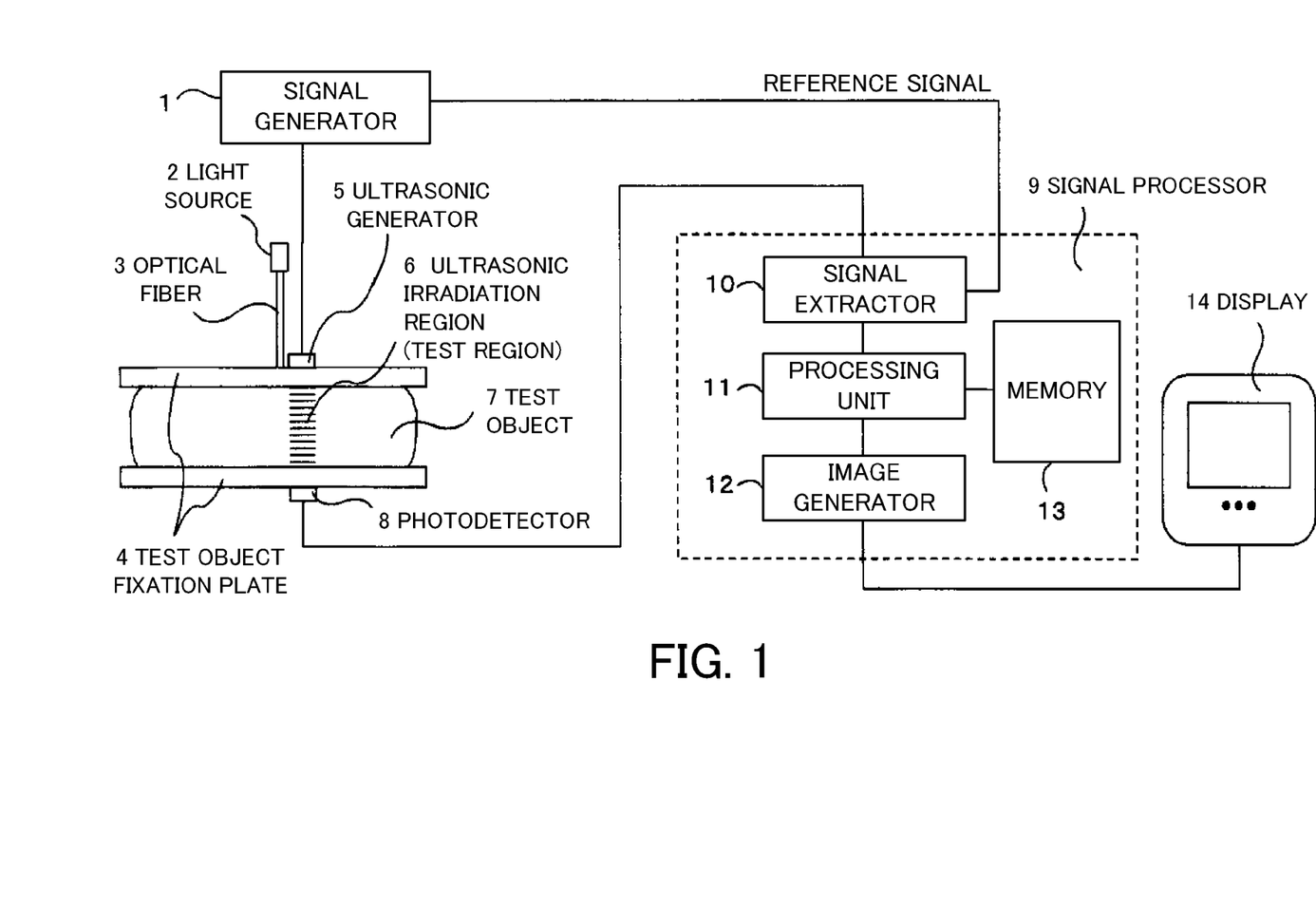
FIG. 1 is a block diagram of a measurement apparatus according to a first embodiment.

FIG. 1 is a block diagram of a measurement apparatus according to a first embodiment. The measurement apparatus is configured to measure a spectroscopic characteristic (absorption-scattering characteristic) in a test object using the acousto-optical tomography ("AOT"), and includes a (first) measurement unit, a signal processor 9, and a display 14.

The (first) measurement unit is configured to irradiate at least three types of ultrasonic waves and light upon a test region 6 in a test object 7. The three types of ultrasonic waves include an ultrasonic wave having a (first) frequency $f_a$ and a (first) amplitude "A," an ultrasonic wave having the frequency $f_a$ and a (second) amplitude $A_1$, and an ultrasonic wave having a (second) frequency $f_{a1}$ and the (first) amplitude "A." The measurement unit is configured to measure modulated light $I_i$ and non-modulated light $I_0$. The modulated light $I_1$ being modulated by the acousto-optical effect caused by an interaction between the light irradiated onto the test region 6 and the ultrasonic wave. The measurement unit includes a signal generator 1 configured to generate a signal, such as a sine wave, a light source 2, an optical fiber 3, a pair of test object fixation plates 4, an ultrasonic generator (ultrasonic transducer array) 5, and a photodetector 8.

The test object 7 is a biological tissue, such as a breast, and an absorption-scattering medium. The test object 7 is lightly pressed and fixed by a pair of test object fixation plates 4 from two directions. The test object fixation plate 4 is optically transparent, and is made of a material that has an acoustic impedance comparatively close to the test object 7.

The light source 2 can generate continuous wave ("CW") light beams having a plurality of wavelengths, a long coherence length (for example, equal to or longer than 1 m), and a constant intensity. The wavelength in the light source is selected among wavelengths in accordance with absorption spectra such as water, lipid, protein, oxyhemoglobin, and deoxyhemoglobin. In one illustration, an appropriate wavelength falls upon a range between 600 to 1,500 nm, because the light can highly transmit due to a small absorption of water that is a main ingredient of the internal biological tissue, and the spectra of the lipid, the oxyhemoglobin, and the deoxyhemoglobin are characteristic. The light source 2 is a semiconductor laser, a wavelength variable laser, etc., configured to generate a plurality of different wavelengths.

The optical fiber 3 guides the light generated from the light source 2 to the test object 7. A condenser optical system configured to efficiently introduce the light from the light source 2 to the end of the optical fiber 3 may be provided before the optical fiber 3. The light incident upon the inside of the test object 7 propagates while repeating the absorptions and the scatterings.

The ultrasonic generator 5 generates a plane ultrasonic wave that propagates towards the opposite photodetector 8. The ultrasonic frequency ranges from about 1 to 10 MHz. The ultrasonic generator 5 includes, for example, a linear array probe. The frequency and the amplitude of the ultrasonic wave generated by the ultrasonic generator 5 can be controlled by the signal processor 9.

The ultrasonic irradiation region 6 generates a sound field in accordance with the ultrasonic frequency and amplitude set by the ultrasonic generator 5. In this region, the sound pressure changes the density of the medium and eventually changes the refractive index of the medium, and displaces the scatters. When the light enters this region, the light phase is modulated with the ultrasonic frequency due to the modulation of the refractive index of the medium and the displacement of the scatterers. This phenomenon is now referred to as an acousto-optical effect.

The photodetector 8 detects modulated light modulated by the acousto-optical effect in the ultrasonic irradiation region 6, non-modulated light that is not modulated in the ultrasonic irradiation region 6, and non-modulated light that passes part other than the ultrasonic irradiation region 6. The photodetector 8 of this embodiment can apply a single sensor, such as a photomultiplier tube ("PMT") and an avalanche photodiode ("APD"), or a multi-sensor, such as a CCD and a CMOS. This embodiment is applicable when a CCD or CMOS is used to measure the modulation depth.

Although not shown in FIG. 1, the optical fiber 3, the ultrasonic generator 5, and the photodetector 8 have a mechanism for two-dimensionally scanning a surface of the test object fixation plate 4 synchronously. The spatial measurement distribution of the test object 7 can be obtained by scanning these units relative to the test object 7.

The signal processor 9 is configured to calculate a modulation depth M that is an intensity of the modulated light $I_1$ divided by an intensity of the non-modulated light $I_0$ for each ultrasonic wave, and at least one of a scattering characteristic and an absorption characteristic of the test region 6 in the test object 7. In that case, the signal processor 9 utilizes a first change rate (ultrasonic amplitude change rate) of the modulation depth M to an amplitude of the ultrasonic wave or an amount corresponding to the first change rate, and a (second) change rate (ultrasonic frequency change rate) of the modulation depth M to a frequency of the one or an amount corresponding to the second change rate. The signal processor 9 analyzes information on the spectroscopic characteristic about the absorption and the scattering in the test object 7, generates an image, and includes a signal extractor 10, a processing unit 11, an image generator 12, and a memory 13.

The signal extractor 10 has a filter function, and separates the modulated light and the non-modulated light from each other. The signal extractor 10 can apply a band-pass filter configured to selectively detect a signal of a specific frequency, and a lock-in amplifier configured to amplify and detect the light of a specific frequency. For example, when the photodetector 8 utilizes a PMT or APD, the signal extractor 10 measures the modulated light $I_1$ and the non-modulated light $I_0$, and the signal processor 11 calculates the modulation depth $M=I_1/I_0$. Alternatively, when the photodetector 8 uses a CCD or a CMOS, an output signal is amplified and AD-converted, and the resultant data is delivered to the processing unit 11. The processing unit 11 calculates the modulation depth M from the speckle contrast with the ultrasonic wave irradiation and without the irradiation. The calculated modulation depth M is stored in the memory 13.

The processing unit 11 calculates concentrations and a ratio of components in the test object that contribute to the absorption of the spectroscopic characteristic. In addition, the processing unit 11 produces distribution data of the spectroscopic characteristic in the test object 7 by mapping data of the calculated spectroscopic characteristic to the data of the ultrasonic irradiated coordinate.

The image generator 12 generates a three-dimensional tomographic image of the test object 7, based on the distribution data of the spectroscopic characteristic in the test object 7 produced by the processing unit 11.

The memory 13 records data generated by the processing unit 11 and an image of a spectroscopic characteristic generated by the image generator 12. The memory 13 may use a data recording device such as an optical disc, a magnetic disc, a semiconductor memory, and a hard disk drive.

The display 14 displays an image generated by the signal processor 9, and uses a display device, such as a liquid crystal display, a CRT, and an organic EL.

Figure 2:
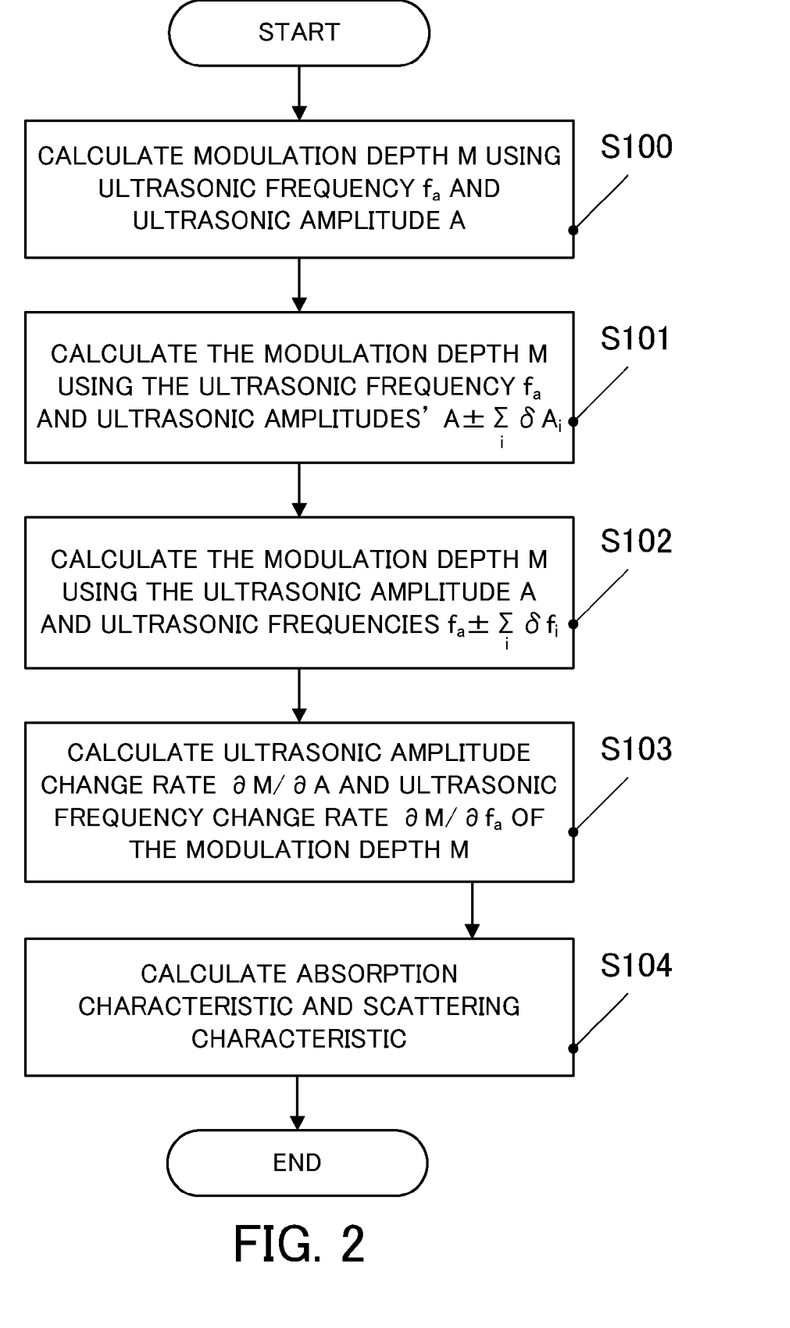
FIG. 2 is a flowchart for explaining an operation of a signal processor shown in FIG. 1.

FIG. 2 shows a measurement (or calculation) procedure by the signal processor 9 (in particular, the processing unit 11) with the light of one wavelength at one ultrasonic irradiation position. In FIG. 2, "S" denotes the step. Initially, in S100, the signal processor 9 controls the ultrasonic generator 5 and measures the modulated light $I_1$ and the non-modulated light $I_0$ with the ultrasonic wave having a frequency $f_a$ and an amplitude "A", and calculates the modulation depth M using the obtained measurement result and the Equation 12.

Next, in S101, the signal processor 9 controls the ultrasonic generator 5 and changes the ultrasonic amplitude to the amplitude $A_1$ near "A" set in S100, maintains other conditions (or maintains the frequency $f_a$), and measures the modulated light $I_1$ and the non-modulated light $I_0$. The signal processor 9 calculates the modulation depth $M_1$ from the obtained measured result and the Equation 12. It is enough to calculate at least one modulation depth with the amplitude $A_1$ different from the amplitude A but modulation depths can be calculated at a plurality of points so as to obtain the change rate of the modulation depth to the amplitude precisely. The measurement data obtained at this time is also stored in the memory 13.

Next, in S102, the signal processor 9 controls the ultrasonic generator 5, changes the ultrasonic frequency to the frequency $f_{a1}$ near $f_a$ set in S100, maintains other conditions (or maintains the amplitude A), and measures the modulated light $I_1$ and the non-modulated light $I_0$. The signal processor 9 calculates the modulation depth $M_2$ from the obtained measured result and the Equation 12. It is enough to calculate at least one modulation depth with the different frequency but modulation depths can be calculated at a plurality of points near $f_a$ so as to obtain the change rate of the modulation depth to the frequency precisely. The measurement result is stored in the memory 13.

Next, in S103, the signal processor 9 uses data obtained in the measurement in S101, and calculates the ultrasonic amplitude change rate $\partial M/\partial A$ of the modulation depth M to the ultrasonic amplitude. In addition, the signal processor 9 uses data obtained in the measurement in S102, and calculates the ultrasonic frequency change rate $\partial M/\partial f_a$ of the modulation depth M to the ultrasonic frequency. Even when these values are not actually calculated and held, necessary values for the Equations 23-26 may be substituted.

Next, in S104, the signal processor 9 calculates the absorption characteristic and the scattering characteristic of the light in the ultrasonic irradiation region 6 using the modulation depth M, the change rate $\partial M/\partial A$ of the modulation depth M to the ultrasonic amplitude and the change rate $\partial M/\partial f_a$ of the modulation depth M to the ultrasonic frequency. While the refractive index changes in the ultrasonic irradiation range 6, the refractive index does not directly affect the absorption or the scatter. In addition, the scattering is vibrated and modulated by the ultrasonic wave but the ultrasonic modulation at this time mainly depends upon the scattering. Thus, only the scattering charactering can be obtained by investigating the ultrasonic change rates, such as the ultrasonic amplitude change rate and the ultrasonic frequency change rate.

A description will now be given of a method of calculating the absorption characteristic and the scattering characteristic using the modulation depth M, the change rate $\partial M/\partial A$ of the modulation depth M to the ultrasonic amplitude, and the change rate $\partial M/\partial f_a$ of the modulation depth M to the ultrasonic frequency.

Initially, since the probability density function p(s) in the Equation 1 also depends upon an absorption coefficient $\mu_a$ [mm$^{-1}$], a scattering coefficient $\mu_s$ [mm$^{-1}$], and an anisotropic parameter g in addition to the optical path length "s", it is described as p(s, $\mu_a$, $\mu_s$, g). In addition, since the correlation part <Es(t)E*s(t+τ)> of the electric field in the Equation 1 is a function that depends upon the scattering coefficient $\mu_s$ the anisotropic parameter g, the ultrasonic amplitude "A" [nm], and the ultrasonic frequency $f_a$ [Hz] in addition to the optical path length "s" and time τ, it is described as h(s, τ, $\mu_s$, g, A, $f_a$). Therefore, the Equation 1 becomes as follows:

$$G_1(\tau) = \int_0^\infty p(s, \mu_a, \mu_s, g) h(s, \tau, \mu_s, g, A, f_a) ds \qquad \text{Equation 13}$$

The modulation depth M is obtained by Fourier-transform of the Equation 13 and by calculating a ratio between the 0-th order component and the first order component. When the Equation 13 is differentiated with the ultrasonic amplitude A, the following equation is obtained:

$$\frac{\partial}{\partial A} G_1(\tau) = \int_0^\infty p(s, \mu_a, \mu_s, g) \frac{\partial}{\partial A} h(s, \tau, \mu_s, g, A, f_a) ds \qquad \text{Equation 14}$$

When the Equation 13 is differentiated with the ultrasonic frequency $f_a$, the following equation is obtained.

$$\frac{\partial}{\partial A} G_1(\tau) = \int_0^\infty p(s, \mu_a, \mu_s, g) \frac{\partial}{\partial f_a} h(s, \tau, \mu_s, g, A, f_a) ds \qquad \text{Equation 15}$$

The three parameters, i.e., the absorption coefficient $\mu_a$, the scattering coefficient $\mu_s$, and the anisotropic parameter "g," can be calculated by using three independent and simultaneous equations from the Equations 13-15. In addition, a separation of the absorption characteristic from the scattering characteristic is often sufficient. In that case, the absorption coefficient $\mu_a$ and the reduced scattering coefficient $\mu_s'$ (=(1−g)$\mu_s$) [mm$^{-1}$] may be separated and calculated using the Equations 13-15.

The major physical factor of the above acousto-optical effect that realizes the AOT results from the refractive index change due to the ultrasonic irradiation and the phase modulation of the light due to the scatter's displacement. Thereby, modulation depth M, which is the signal of AOT, can be sensitively influenced by the scattering characteristics. Hence, the influence of the scattering can be sensitively recognized by changing the irradiated ultrasonic parameter and by measuring a change of the signal. When the above condition is added to the conventional measurement of only the modulation depth obtained by the Fourier transformation of the Equation 13 so as to solve them simultaneously, the absorption and the scattering can be comparatively easily separated in the AOT.

A description will now be given of a method of separating the absorption coefficient and the scattering coefficient from the autocorrelation function of the Equation 2. The ultrasonic frequency used for the biological measurements and medial examinations is about MHz, and each hyperbolic sine function in the Equations 2 and 3 can be linearly developed and approximated in the ultrasonic amplitude (energy) below the ultrasonic irradiation safety standard of a diagnosis. In addition, due to $Z_0 \ll 1$, the following equation is obtained when the terms of the second or higher order are ignored:

$$1 - G_1(\tau) = \frac{L_0^2}{6} \frac{S_U + S_B + \mu_a}{D} \qquad \text{Equation 16}$$

As apparent from the Equation 16, a sum of $S_u$ that indicates the ultrasonic influence and the absorption coefficient $\mu_a$ is contained and these parameters are independent. Hence, the ultrasonic amplitude "A" or the ultrasonic frequency $f_a$ in the Equation 16 does not depend upon the absorption characteristic, but depends upon only the scattering characteristic. As described later, the left side of the Equation 16 and the modulation depth M are correlated, it is considered that the change rates of the modulation depth M to the ultrasonic amplitude "A" and the ultrasonic frequency $f_a$ reflect only the scattering characteristic eventually.

Therefore, the scattering characteristic can be calculated by measuring the above change rates of the modulation depth M. Once the scattering characteristic is calculated, the absorption characteristic can be calculated. A description will now be given of calculations of the absorption characteristic and the scattering characteristic in accordance with this model. The following equation is obtained when τ=Ta/2 is substituted and arranged in the measurement system in which an effect of the Brownian movement is negligible:

$$1 - G_1(T_a/2) = \frac{L_0^2}{6D} \left\{ \frac{1}{2}(2n_0 k_0 A)^2 (\delta_n + \delta_d) + \mu_a \right\} \qquad \text{Equation 17}$$

When the Equation 17 is differentiated by "A" and arranged, the following equation can be obtained:

$$\frac{1}{2A} \frac{\partial}{\partial A}[1 - G_1(T_a/2)] = \qquad \text{Equation 18}$$

$$(n_0 k_0 L_0)^2 \mu_s' \left( \frac{\eta^2 k_a^2 \text{Re}[\hat{j}(\hat{I} - \hat{j})^{-1}]_{0,0}}{\mu_s} + \frac{\mu_s'}{3} \right)$$

The following equation is obtained from the Equations 17 and 18:

$$\frac{A}{2} \frac{\partial}{\partial A}[1 - G_1(T_a/2)] + \frac{L_0^2}{2} \mu_a \mu_s' = [1 - G_1(T_a/2)] \qquad \text{Equation 19}$$

On the other hand, the (0, 0) component of a matrix $\hat{j}(\hat{I}-\hat{j})^{-1}$ can be expressed by the following equation:

$$[\hat{j}(\hat{I} - \hat{j})^{-1}]_{0,0} = -\frac{1}{i2k_a l \Big/ \log\left(\frac{1 - ik_a l}{1 + ik_a l}\right) + 1} \qquad \text{Equation 20}$$

The Equation 20 can be approximated as follows when the above ultrasonic frequency and the mean free path in the biological tissue are considered:

$$[\hat{J}(\hat{I}-\hat{J})^{-1}]_{0,0} \approx \frac{3}{(k_a l)^2} + \frac{4}{5} \quad \text{Equation 21}$$

When the Equation 21 is substituted for δn in the Equation 17 and the result is arranged with a relationship ka=(2π/va)fa and differentiated by fa, the following equation is obtained:

$$\frac{\partial}{\partial f_a}[1 - G_1(T_a/2)] = \frac{2}{5}\left(\frac{4\pi n_0 k_0 AL\eta}{v_a}\right)^2 \frac{\mu'_s}{\mu_s} f_a \quad \text{Equation 22}$$

When the Equations 17, 18, 22, and 21 are solved with respect to the reduced scattering coefficient μs' and the absorption coefficient μa, the following equations are obtained:

$$\mu'_s = \frac{1}{n_0 k_0 AL_0}\sqrt{\frac{\frac{\partial}{\partial A}[1-G_1(T_a/2)]A - \frac{\partial}{\partial f_a}[1-G_1(T_a/2)]f_a}{\frac{1}{3} + \frac{2}{5}\frac{(2\pi n_0 k_0 AL_0 \eta/v_a)^2 f_a}{\frac{\partial}{\partial f_a}[1-G_1(T_a/2)]}}} \quad \text{Equation 23}$$

$$\mu_a = \frac{2}{L_0^2 \mu'_s}\left([1-G_1(T_a/2)] - \frac{\partial}{\partial A}[1-G_1(T_a/2)]\frac{A}{2}\right) \quad \text{Equation 24}$$

Figure 3:
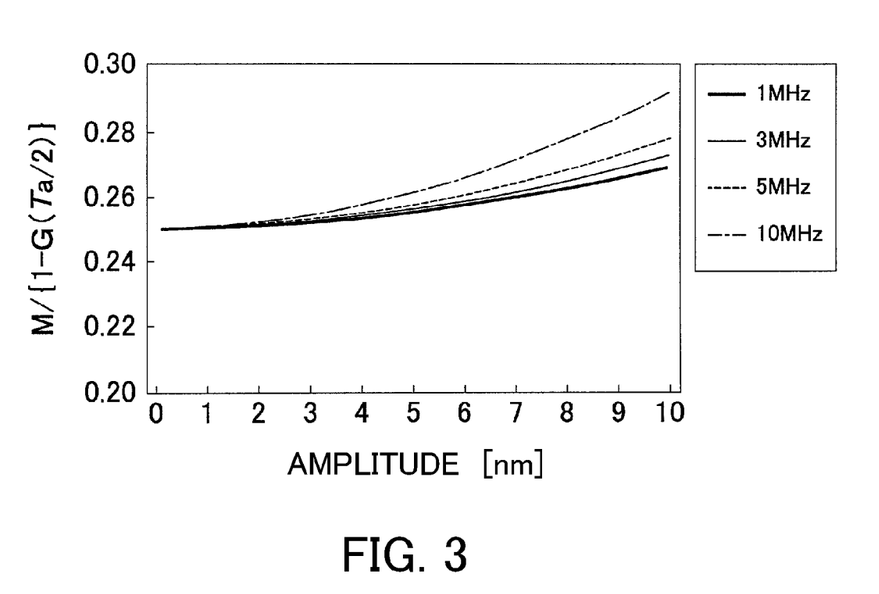
FIG. 3 is a graph showing a relationship between an amplitude and $M/\{1-G_1(T_a/2)\}$.

In addition, as shown in FIG. 3, in the ranges of the absorption coefficient and the scattering coefficient in the biological tissues and in the range of the ultrasonic amplitude "A" equal to or smaller than 1 nm, the modulation depth M is proportional to [1−G1(Ta/2)]. Hence, the Equations 23 and 24 can be finally expressed as follows using the modulation depth M. In addition, ∂[1−G1(Ta/2)]/∂A is an amount corresponding to ∂M/∂A. Similarly, ∂[1−G1(Ta/2)]/∂fa is an amount corresponding to ∂M/∂fa.

$$\mu'_s = C_s \frac{1}{n_0 k_0 AL}\sqrt{\frac{\left(\frac{\partial}{\partial A}M\right)A - \left(\frac{\partial}{\partial f_a}M\right)f_a}{\frac{1}{3} + \frac{2}{5}\frac{(2\pi n_0 k_0 AL\eta/v_a)^2 f_a}{\left(\frac{\partial}{\partial f_a}M\right)}}} \quad \text{Equation 25}$$

$$\mu_a = C_a \frac{2}{L^2 \mu'_s}\left(M - \left(\frac{\partial}{\partial A}M\right)\frac{A}{2}\right) \quad \text{Equation 26}$$

Cs and Ca are proportional constants. When the test object to be measured is sufficiently thick, L0 may be replaced with L. Based on the Equations 25 and 26, the modulation depth M, the change rate ∂M/∂A of the modulation depth M to the ultrasonic amplitude, and the change rate ∂M/∂fa of the modulation depth M to the ultrasonic frequency, a value proportional to the reduced scattering coefficient μs' and a value proportional to absorption coefficient μa can be obtained. The former corresponds to the scattering characteristic in the test region, and the latter corresponds to the absorption characteristic in the test region.

This embodiment calculates the ultrasonic amplitude change rate and the ultrasonic frequency change rate of the modulation depth M, and then the scattering characteristic of the test region 6 in the test object 7 by utilizing the calculation result. In addition, this embodiment calculates the absorption characteristic in the test object by utilizing the calculated scattering characteristic in, as in the Equations 24 or 26.

The Equations 23-26 are met as long as the test object has a comparatively simple shape but when the test object has a complex shape, another condition possibly needs to be added. Therefore, the scattering characteristic and the absorption characteristic are not necessarily limited to those defined in the Equations 23-26.

Even when the ultrasonic amplitude A is 1 nm or larger, the scattering characteristic and the absorption characteristic can be calculated by using a correction table or a polynomial, which shows a relationship between the modulation depth M and [1−G1(Ta/2)] in FIG. 3.

Thus, this embodiment calculates the change rate ∂M/∂A of the modulation depth M to the ultrasonic amplitude, and the change rate ∂M/∂fa of the modulation depth M to the ultrasonic frequency in addition to the modulation depth M that is conventionally measured. In addition, this embodiment utilizes the Equations 25 and 26 to measure the absorption characteristic proportional to the absorption coefficient and the scattering characteristic proportional to the reduced scattering coefficient and to separate them from each other.

U.S. Pat. No. 6,041,248 sweeps the ultrasonic frequency for measurements so as to improve the S/N ratio and the resolution in the ultrasonic traveling direction, but does not obtain the dependency of the modulation depth upon the ultrasonic frequency unlike this embodiment or does not separate the absorption characteristic from the scattering characteristic.

Thus, in S104 in FIG. 2, the signal processor calculates the absorption characteristic and the scattering characteristic of the ultrasonic irradiation region 6 using the Equations 25 and 26. When the signal processor 9 repeats the flow shown in FIG. 2 for each of the wavelengths of the light source 2, the signal processor 9 can obtain the spectroscopic information relating to the absorption and scatting characteristics. Moreover, when the signal processor 9 scans positions of the optical fiber 3, the ultrasonic generators, and the photodetector 8 and repeats the flow shown in FIG. 2 at a different position of the ultrasonic irradiation region 6, the signal processor 9 can obtain spatial distributions of the scattering characteristic and the absorption characteristic. The processing unit 11 maps the positional coordinate in a plane of the ultrasonic irradiation region 6 in the test object fixation plate 4 to the scattering characteristic and the absorption characteristic, and the image generator 12 visualizes the data as an image. Thereby, two-dimensional spatial distributions of the scattering characteristic and the absorption characteristic in the ultrasonic irradiation region 6 can be obtained, and the image is displayed on the display 14. The scattering characteristic and the absorption characteristic may be normalized by maximum values in their spatial distributions or by measurement values that has previously obtained with the known and calibrated equivalent scattering coefficient and absorption coefficient.

In addition, the processing unit 11 calculates, based on the absorption characteristics obtained with a plurality of wavelengths, concentrations of the major components of the test object 7, such as oxyhemoglobin, deoxyhemoglobin, water, fat, and collagen, and functional information, such as metabolism of the hemoglobin. The functional information is mapped to the positional coordinate of the ultrasonic irradiation region 6 similar to the above description. The image generator 12 generates image data for visualizations, and the display 14 displays the image data.

When the scattering characteristic of the test object 7 can be considered approximately uniform and the internal distribution of the absorption characteristic or the ratio of components, etc. is addressed for visualizations, the scattering characteristic obtained in the Equation 25 is processed as an internal parameter for calculating the absorption characteristic. At this time, the display 14 displays the spatial distribution of the absorption characteristic or the ratio of components.

This embodiment precisely separates the absorption characteristic and the scattering characteristic from each other with high resolution for two-dimensionally specifying the ultrasonic irradiation regions, and can precisely measure a ratio of components and the functional information.

Second Embodiment

Figure 4:
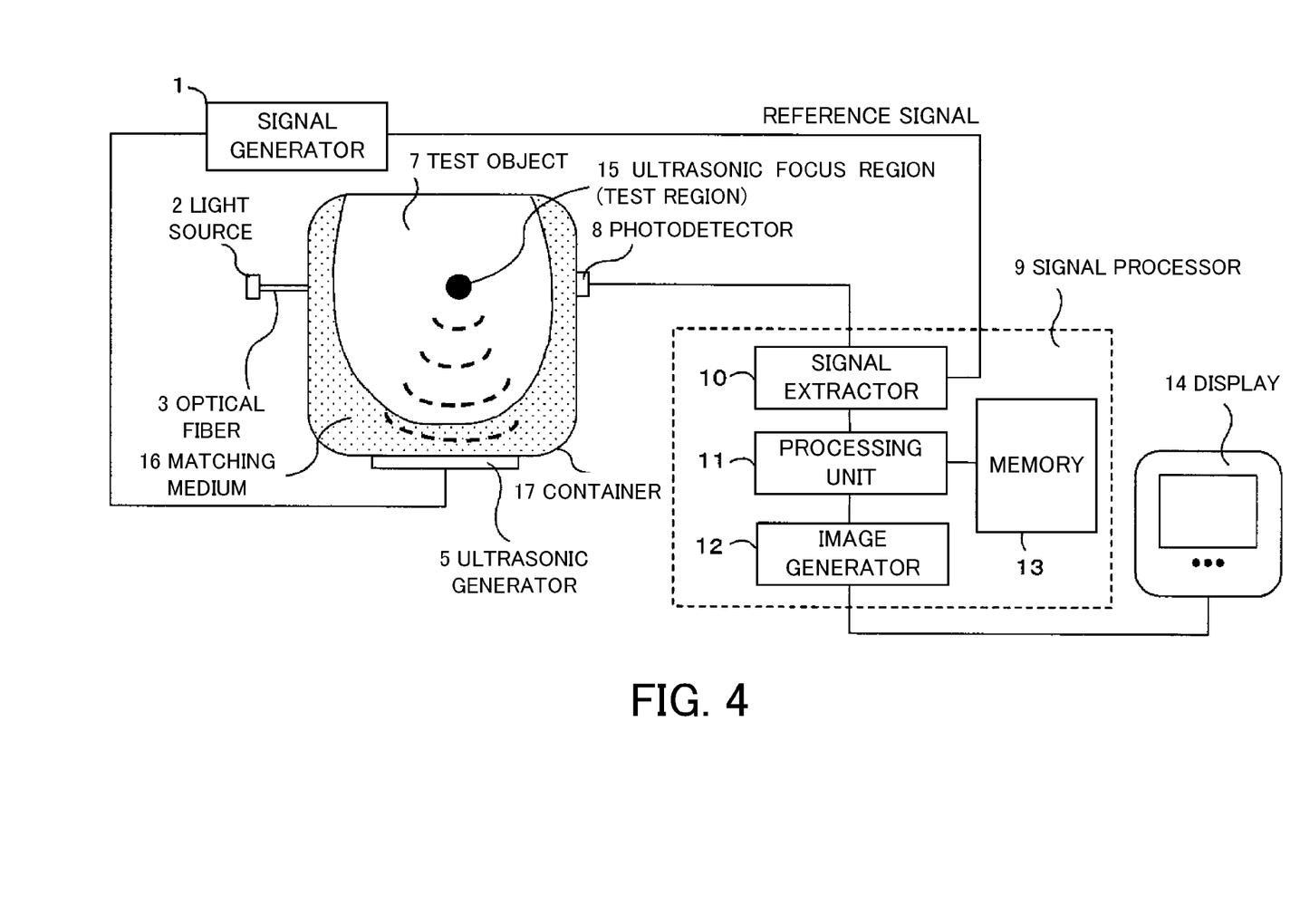
FIG. 4 is a block diagram of a measurement apparatus according to a second embodiment.

FIG. 4 is a block diagram of a measurement apparatus according to a second embodiment. The signal processor 9 and the display 14 are the same as those of the first embodiment. In this embodiment, the test object 7 is housed in the container 17. A homogeneous medium (matching material) 16 having a known characteristic is filled in a space between the test object 7 and the container 17, and has a refractive index and a scattering coefficient to the light and an acoustic characteristic to the ultrasonic wave equivalent to the test object 7. The ultrasonic generator 5 includes an ultrasonic focus mechanism configured to focus the ultrasonic wave upon an ultrasonic focus region 15 in the test object 7. The ultrasonic focus region 15 is a test region of the AOT.

Figure 5:
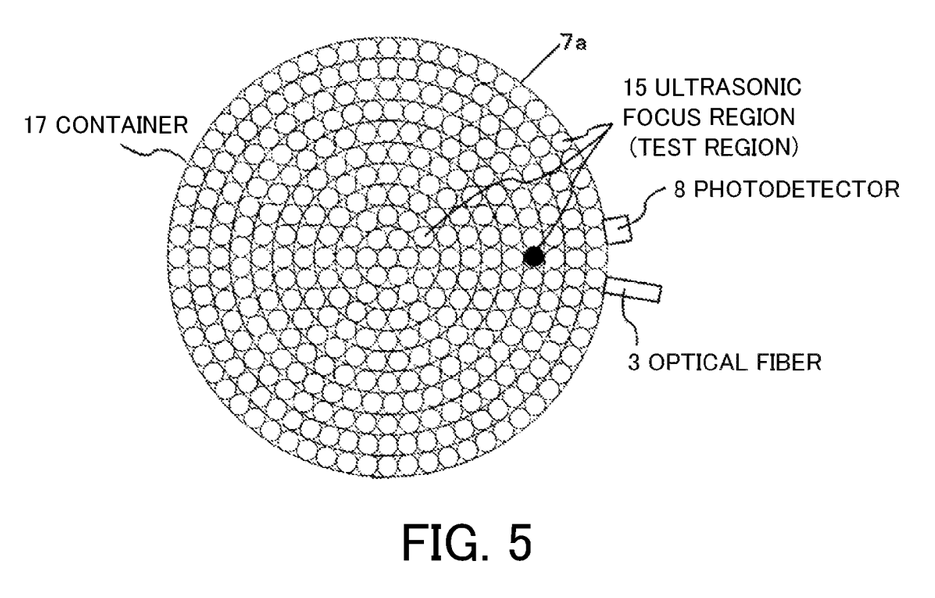
FIG. 5 is a sectional view of a container shown in FIG. 4.

FIG. 5 is a lateral sectional view of the container 17 shown in FIG. 4. For simplicity, FIG. 5 shows that the test object 7 spreads over the inside of the container 17 in one section, and a front layer 7a as the outermost surface of the test object 7 accords with the external surface of the container 17. Of course, the matching medium 16 may exist between the test object 7 and the container 17. The ultrasonic focus regions 15 are concentrically set test regions in the test object 7, and include a black dot that is a target test object whose spectroscopic characteristic is now being sought. This embodiment sequentially scans a position of the ultrasonic focus region 15 in the container 17 in measurements, as shown in FIG. 5. Thereby, the ultrasonic focus regions 15 can three-dimensionally cover the inside of the container 17 entirely. The light incident position of the optical fiber 3 and the detection position of the photodetector 8 are configured to move with the position of the ultrasonic focus region 15. Both constitute a reflectance measurement system configured to measure the backscattering light, as shown in FIG. 5, and a distance between the optical fiber 3 and the photodetector 8 is made larger as the position of the ultrasonic focus region 15 approaches to the center of the container 17.

Thus, S100 to S102 in the flow shown in FIG. 2 are performed for all the test regions (the ultrasonic focus regions 15) that are set in the container 17, and the measured modulation depths are stored in the memory 13. The measurement condition, such as the positional coordinate of the ultrasonic focus region 15 and the ultrasonic irradiation condition, is also stored in the memory 13. When acquisitions of data of all test regions are completed, the processing unit 11 analyzes the data.

In this embodiment, as shown in FIG. 5, the modulation depth M that occurs in the ultrasonic focus region 15 depends upon the influence of the scatterings and absorptions on the propagation path of the light from the optical fiber 3 to the ultrasonic focus area 15 and the similar influence on the propagation path of the light from the ultrasonic focus region 15 to the photodetector 8. For example, when there is an object that exhibits a higher absorption between the ultrasonic focus region 15 and the photodetector 8, it has a smaller modulation depth M to be measured. Thus, in measuring the modulation depth M, the influence of the crosstalk needs to be considered.

On the other hand, the ultrasonic frequency change rate and the ultrasonic amplitude change rate of the modulation depth M locally occur in the ultrasonic focus region 15, and are irrelevant to the influence of the propagation path from the optical fiber 3 to the ultrasonic focus region 15 or the influence of the propagation path from the ultrasonic focus region 15 to the photodetector 8. Although the measured modulation depth M fluctuates under the influence of the crosstalk, the ultrasonic frequency change rate and the ultrasonic amplitude change rate of the modulation depth M are stored without receiving the influence of the crosstalk. By using this fact, a relative distribution of the scattering characteristic can be calculated without considering the influence of the crosstalk, because the Equation 25 clearly utilizes the ultrasonic frequency change rate and the ultrasonic amplitude change rate of the modulation depth M to calculate the scattering characteristic.

Based on the foregoing theory, the processing unit 11 reads out the measurement data and the measurement condition from the memory 13, and calculates the ultrasonic frequency change rate and the ultrasonic amplitude change rate of the modulation depth M. Then, the processing unit 11 calculates the scattering characteristic in accordance with the Equation 25 using these values. The scattering characteristic is correlated with the position of the ultrasonic focus region 15, and the scattering characteristics in the container 17 are mapped. The image generator 12 visualizes the mapping result and generates the image data. The display 14 displays the image data.

The scattering coefficient can be calculated by previously calibrating the parameter, such as a proportional constant in the Equation 25 using the homogeneous matching medium 16 having a known scattering characteristic.

Rather than the reflectance measurement system, a transmittance measurement system configured to detect the light that transmits the test object may be used.

This embodiment can precisely calculate the distribution of the scattering characteristic in the test object with a spatial resolution set with the ultrasonic focus regions 15.

Third Embodiment

Third embodiment calculates the absorption characteristic as well as the scattering characteristic similar to the second embodiment, using the measurement apparatus shown in FIG. 4 which is the same as that of the second embodiment. The measurement apparatus of the third embodiment sequentially scans the position of the ultrasonic focus region 15 in the container 17 for such measurements that the ultrasonic focus regions 15 can three-dimensionally cover the inside of the container 17 entirely. The light incident position of the optical fiber 3 and the detection position of the photodetector 8 are configured to move in accordance with the position of the ultrasonic focus region 15, and both constitute a reflectance measurement system configured to measure the backscattering light similar to the second embodiment. A distance between the optical fiber 3 and the photodetector 8 is made larger as a position of the ultrasonic focus region 15 approaches to the center of the container 17.

Initially, by using the same method as that of the second embodiment, S100 to S102 in the flow shown in FIG. 2 are performed for all the test regions (the ultrasonic focus regions 15) set in the container 17. Next, similar to the second embodiment, the scattering characteristics is calculated for each of all test regions. The data is mapped to the positional coordinate of the ultrasonic focus region 15 and stored in the memory 13. Similar to the second embodiment, the parameters, such as proportional constants in FIGS. 25 and 26, may be previously calibrated by measuring the homogeneous matching medium 16 having a known characteristic.

Next, the processing unit 11 reads out the measurement data of the outermost region of the container 17, the modulation depth M, the ultrasonic amplitude change rate ∂M/∂A of the modulation depth M, and the measurement values of the scattering characteristic, from the memory 13. The signal processor 9 calculates the absorption characteristic from the Equation 26 using these values. This is performed for the entire outermost regions of the container 17 in the sectional view shown in FIG. 5 to calculate the absorption characteristics and the scattering characteristics of the outermost regions. At this time, it is understood that the equations of the absorption characteristic, such as the Equations 24 and 26, contains M or [1−G1(Ta/2)] and the absorption characteristic is subject to the crosstalk. This embodiment recursively calculates the absorption characteristic of the test region.

Figure 6:
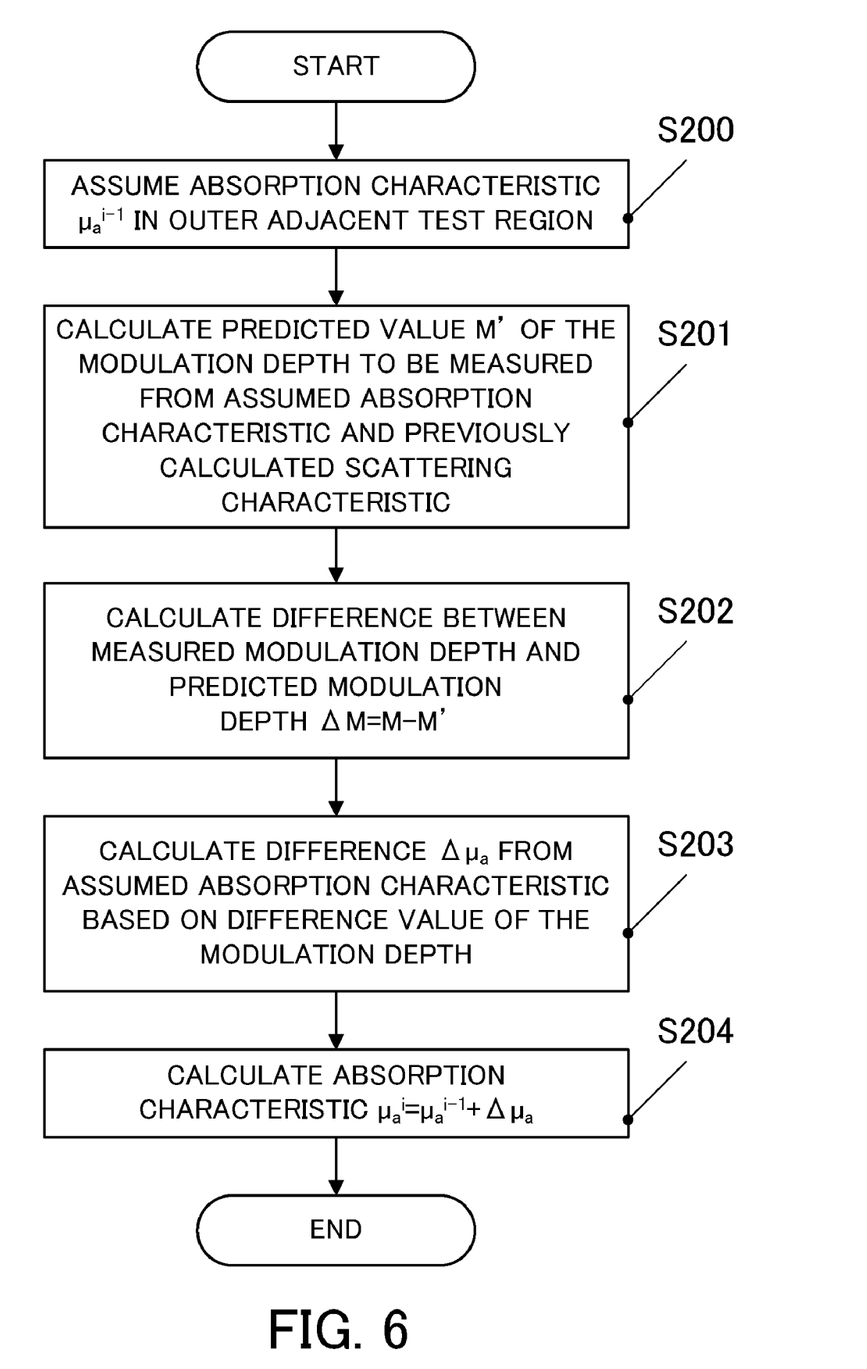
FIG. 6 is a flowchart for explaining an operation of a signal processor in a measurement apparatus according to a third embodiment.
Figure 7:
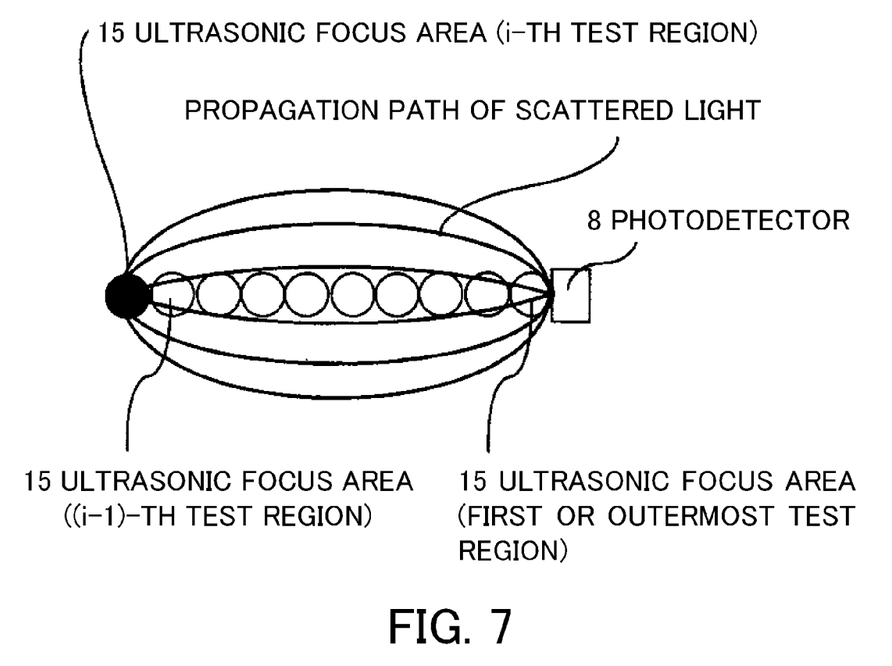
FIG. 7 is a schematic plane view showing propagation paths of the light that propagates between a current ultrasonic focus region and a photodetector shown in FIG. 5 and test regions arranged on the propagation paths.

The data inside of the outermost regions in the container 17 is analyzed in accordance with a flow shown in FIG. 6. Initially, as shown in FIG. 7, the signal processor 9 reads out the absorption characteristic of the outermost region adjacent to a test region that is a target ultrasonic focus region 15 of the analysis of S200 in the measurement time, and assumes that it is the absorption characteristic of the test region.

In S201, the signal processor 9 calculates predicted modulation depth M' with the Equations 2-12 using the absorption characteristic assumed in S200 and the previously measured scattering characteristic. At this time, the signal processor 9 calculates the predicted modulation depth M' by considering the propagation effect using the Monte Carlo simulation, transportation equation, or the diffusion equation for the propagation path from the test region to the photodetector 8.

In S202, the signal processor 9 calculates a difference ΔM between the measured modulation depth M (actually measured value) and the predicted modulation depth M' (predicted value) calculated in S201. Since the ultrasonic amplitude change rate of the modulation depth M is not subject to the influence of the propagation path, ΔM calculated in S202 contributes to the absorption characteristic as shown in Equation 27. In S203, the signal processor 9 calculates a difference Δμa from the assumed absorption characteristic using Equation 27.

$$\Delta \mu_a = C_a \frac{2}{L^2 \mu_s'} \left( \Delta M - \left( \frac{\partial}{\partial A} M \right) \frac{A}{2} \right) \quad \text{Equation 27}$$

In S204, a difference of the absorption characteristic obtained from the Equation 27 is sequentially corrected, and the absorption characteristic in the test region is calculated.

$$\mu_a^i = \mu_a^{i-1} + \Delta \mu_a \quad \text{Equation 28}$$

Thus, the flow from S200 to S204 is repeated and the absorption characteristic is recursively calculated from the outermost region to the center in the container 17. All measurement data is read out, and the recursive calculation continues until the analysis of the flow ends.

Similar to the second embodiment, the obtained absorption characteristic and scattering characteristic are mapped to the positional coordinate to provide three-dimensional data of the distributions of the absorption characteristic and the scattering characteristic in the test object 7 in the container 17. Since the absorption characteristic depends upon the wavelength, the functional information, such as the major component and metabolism in the test object 7, can also be mapped as in the first embodiment.

Fourth Embodiment

Figure 8:
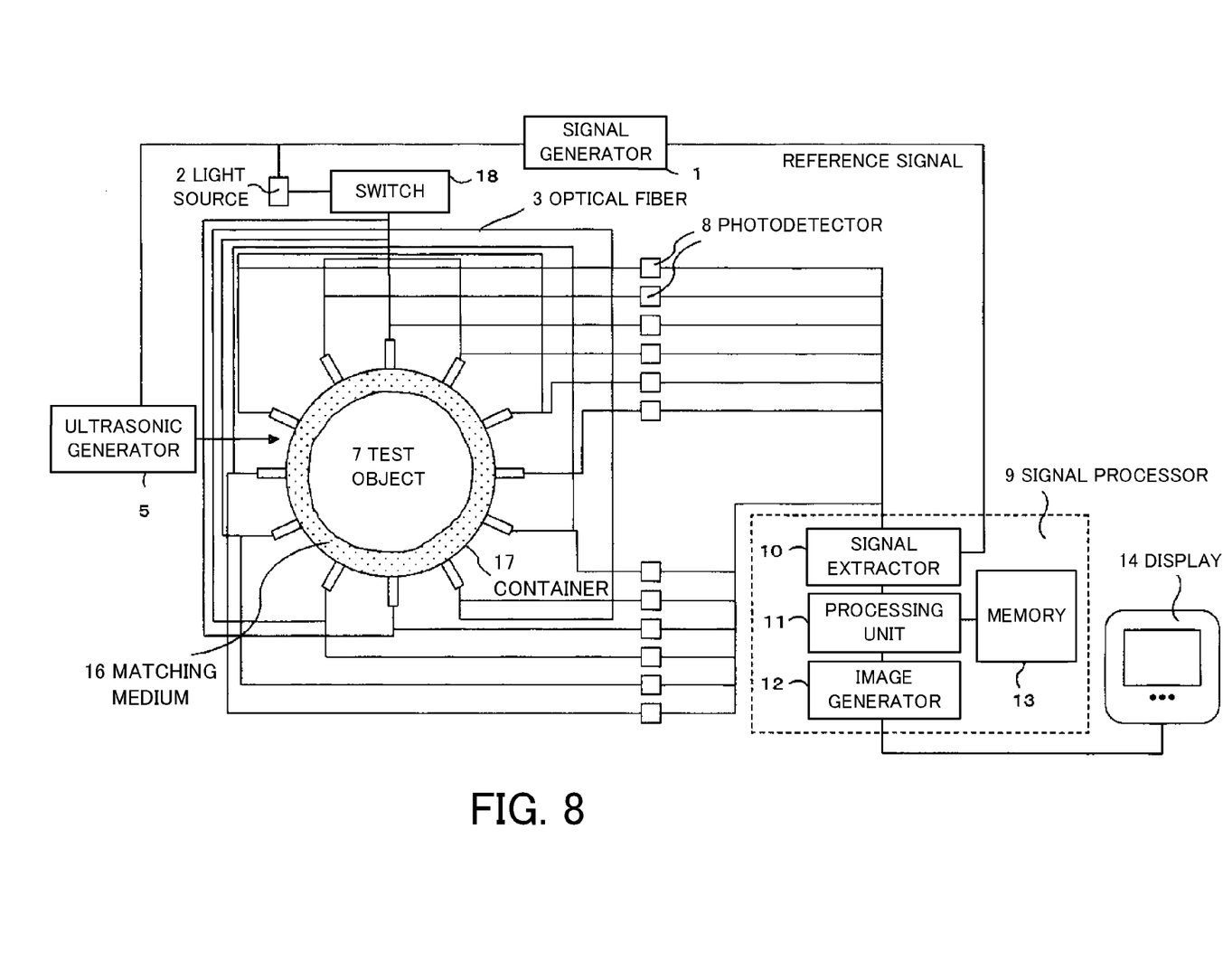
FIG. 8 is a block diagram of a measurement apparatus according to a fourth embodiment.

FIG. 8 is a block diagram of a measurement apparatus according to a fourth embodiment. This embodiment includes two measurement units, one of which (second measurement unit) measures a spectroscopic characteristic of a test object 7 using a diffused optical tomography ("DOT"). The measurement unit using the DOT measures the spectroscopic characteristic in the biological tissue using the light from a visible range to a near infrared range, and visualizes the spatial distribution of the spectroscopic characteristic, the major components, and metabolism information in the biological tissue.

A signal generator 1 generates a sine signal having a frequency "f". The sine signal generated by the signal generator 1 is used to drive a light source 2. In general, in a biological measurement, the intensity of the light is modulated with the sine wave of dozens of MHz to hundreds of MHz. The light source 2 uses one described in the first embodiment, etc.

The intensity-modulated light having the frequency "f" is radiated from the light source 2, and guided to an optical fiber 3. The optical fibers 3 are connected to the side surface of the container 17, and a switch 18 is arranged between the container 17 and each optical fiber 3.

The switch 18 has an opening and closing function, such as a shutter, and is operated so that the light from the light source 2 enters one fiber 3 among the "n" fibers 3 and the light from the light source 2 can be shielded from the other (n−1) fibers 3. The (n−1) fibers 3 introduce to the photodetectors 8 the diffused light that has been radiated from the side surface of the container 17, and passed the test object 7 and the matching material 16. The switch 18 shields the optical path to the photodetector 8 from the optical fiber 3 configured to guide the light from the light source 2 to the container 17. One fiber that introduces the light from the light source 2 to the container 17 is exclusive to the (n−1) fibers 3 configured to introduce the diffused light from the container 17 to the photodetectors 8.

The signal detected by the photodetector 8 is transmitted to the signal extractor 10. The signal extractor 10 compares a signal sent as a reference signal from the signal generator 1 with the signal detected by the photodetector 8, and calculates the amplitude and phase of the modulated signal. This is repeated for all (n−1) signals.

The memory 13 stores the data concerning the amplitude and the phase calculated by the signal extractor 10, as well as the measurement condition, such as a fiber 3 used as a light source is also stored in the memory 13. The measurement is repeated "n" times so that each of all "n" fibers can become a light source, and all measurement data is stored in the memory 13. Data obtained by the second measurement unit will be referred to as second measurement data.

The optical fibers may be three-dimensionally arranged on the side surface of the container 17 or a module in which the optical fibers are two-dimensionally arranged may be scanned along the side surface the container 17 in the longitudinal direction so as to obtain the three-dimensional data.

While this embodiment describes one example of the DOT measurement method, the present invention is not limited to this embodiment and may use a measurement method using a time resolution method.

The other measurement unit (first measurement unit) measures the spectroscopic measurement of the test object 7 using the AOT. The light source 2 emits the CW light. Similar to the above description, the light from the light source 2 is guided to the optical fiber 3, and the switch 18 selects one optical fiber 3 as a light source. The light from the light source 2 enters the side surface of the container 17 via the selected optical fiber 3.

The signal generator 1 drives an ultrasonic generators. The ultrasonic generator 5 has an ultrasonic focusing mechanism.

The photodetector 8 simultaneously detects the modulated light that has passed the ultrasonic focus region 15 and been modulated by the ultrasonic wave, and the non-modulated light that has not modulated by the ultrasonic wave. The signal extractor 10 measures the modulation depth M similar to the first embodiment.

The first embodiment unit measures the absorption characteristic and the scattering characteristic of the ultrasonic focus region 15 in accordance with the flow of FIG. 2. The ultrasonic focus region 15 is set as a test region at one or more arbitrary positions in the container 17, and its absorption characteristic and scattering characteristic are measured. Data thus obtained by the first measurement unit is referred to as first measurement data. The first measurement data is stored with the measurement in the memory 13 condition as well as the second measurement data.

When the measurement by the first measurement unit and the measurement by the second measurement unit end, the processing unit 11 reads out the data from the memory 13 to reconstruct an image.

The image reconstruction uses the second measurement data and a generally known technique, such as a model based on a diffusion equation, a light propagation model through the Monte Carlo simulation, and a transport equation.

This embodiment assumes a distribution of the spectroscopic characteristic in the test object, and changes the assumption so that a difference between a predicted value of the spectroscopic characteristic obtained from the assumption and a measurement result by the second measurement unit can fall within a permissible range. In the step of obtaining the optimal solution by changing the assumption, the first measurement data expresses local absorption characteristic and scattering characteristic in the test region, and is used for an initial condition or a solution for a local position when the image is reconstructed with the second measurement data.

Use of the first measurement data for the condition of the image reconstruction can limit the degree of freedom of the solution in the ill-posed problem that is a problem of the DOT. Thereby, the absorption characteristic and the scattering characteristic of the test object 7 can be precisely measured or a distribution of functional information, such as a major component and a metabolism, in the test object 7 can be precisely measured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims a foreign priority benefit based on Japanese Patent Application 2008-237027, filed on Sep. 16, 2008, which is hereby incorporated by reference herein in its entirety as if fully set forth herein.

What is claimed is:

1. A measurement apparatus configured to measure a spectroscopic characteristic in an object, said measurement apparatus comprising:
    a first measurement unit configured to irradiate the object with at least three types of ultrasonic waves and light, the at least three types of ultrasonic waves including a first ultrasonic wave having a first frequency and a first amplitude, a second ultrasonic wave whose frequency equals the first frequency and having a second amplitude different from the first amplitude, and a third ultrasonic wave having a second frequency different from the first frequency and having an amplitude that equals the first amplitude, and
    to measure non-modulated light and modulated light that has been modulated by an acousto-optical effect caused by an interaction between the light and the ultrasonic waves irradiated onto the object; and
    a signal processor configured to calculate:
        a first modulation depth, which is a ratio between an intensity of non-modulated light and an intensity of the modulated light when the first ultrasound wave is irradiated,
        a second modulation depth, which is a ratio between the intensity of non-modulated light and an intensity of the modulated light when the second ultrasonic wave is irradiated, and
        a third modulation depth, which is a ratio between the intensity of the non-modulated light and an intensity of the modulated light when the third ultrasonic wave is irradiated, and
    to calculate a scattering characteristic and an absorption characteristic in the object on the basis of:
        a change rate of a modulation depth to a change of the amplitude of the ultrasonic wave based on a change between the first modulation depth and the second modulation depth and a change between the first amplitude and the second amplitude; and
        a change rate of a modulation depth to a change of the frequency of the ultrasonic wave based on the change between the first modulation depth and the third modulation depth and a change between the first frequency and the second frequency.

2. The measurement apparatus according to claim 1, wherein said signal processor calculates the change rate of the modulation depth to the change of the amplitude of the ultrasonic wave based on a difference between the first modulation depth and the second modulation depth and a difference between the first amplitude and the second amplitude, and calculates the change rate of the modulation depth to the change of the frequency of the ultrasonic wave based on the difference between the first modulation depth and the second modulation depth and the difference between the first amplitude and the second amplitude.

3. The measurement apparatus according to claim 2, wherein said signal processor utilizes the scattering characteristic that has been calculated, to calculate the absorption characteristic in the object.

4. The measurement apparatus according to claim 1, wherein said signal processor calculates the absorption characteristic and based on the absorption characteristic that has been calculated, calculates a concentration and a ratio of components in the object which contribute to absorption.

5. The measurement apparatus according to claim 1, wherein said signal processor maps a coordinate of the object to the at least one of the scattering characteristic and the absorption characteristic of the object, and generates image data to visualize a mapping result, and
    wherein said measurement apparatus further includes a display configured to display the image data.

6. The measurement apparatus according to claim 1, wherein said signal processor calculates the scattering characteristic and the absorption characteristic in a first test region among a plurality of test regions that are arranged on a propagation path of the light from the first test region to a second test region among the plurality of test regions, the first test region being closest to a front surface of the object and adjacent to detection position, and wherein said signal processor calculates a scattering characteristic and an absorption characteristic in the second test region by utilizing the scattering characteristic and the absorption characteristic in the first test region to recursively correct scattering characteristics and absorption characteristics of the plurality of test regions on the propagation path sequentially from the first test region to the second test region.

7. The measurement apparatus according to claim 1, further comprising a second measurement unit configured to measure the spectroscopic characteristic in the object using diffused optical tomography, wherein said signal processor provides an assumption of distributions of the absorption characteristic and the scattering characteristic in the object, and executes an image reconstruction by changing the assumption so that a difference between a predicted value obtained from the assumption and an actually measured value of a measurement by said second measurement unit can fall within a permissible range, and wherein said signal processor utilizes at least one of the absorption characteristic and the scattering characteristic obtained from a measurement result provided by said first measurement unit for an initial condition or a solution for a local position of the image reconstruction.

8. A measurement method configured to measure a spectroscopic characteristic in an object, said measurement method comprising the steps of:

measuring modulated light and non-modulated light as a result of irradiating the object with at least three types of ultrasonic waves and light, the at least three types of ultrasonic waves including a first ultrasonic wave having a first frequency and a first amplitude, a second ultrasonic wave whose frequency equals the first frequency and which has a second amplitude different from the first amplitude, and a third ultrasonic wave having a second frequency different from the first frequency and having an amplitude that equals the first amplitude, and the modulated light being modulated by an acousto-optical effect caused by an interaction between the light and the ultrasonic waves irradiated onto the object; and calculating a first modulation depth, which is a ratio of between an intensity of non-modulated light and an intensity of the modulated light when the first ultrasound wave is irradiated, a second modulation depth, which is a ratio between the intensity of non-modulated light and an intensity of the modulated light when the second ultrasonic wave is irradiated, a third modulation depth, which is a ratio between the intensity of the non-modulated light and an intensity of the modulated light when the third ultrasonic wave is irradiated, and calculating a scattering characteristic and an absorption characteristic in the object on the basis of:

a change rate of a modulation depth to a change of the amplitude of the ultrasonic wave based on a change between the first modulation depth and the second modulation depth and a change between the first amplitude and the second amplitude, and a change rate of a modulation depth to a change of the frequency of the ultrasonic wave based on the change between the first modulation depth and the third modulation depth and a change between the first frequency and the second frequency.

* * * * *